(12) United States Patent
Mande et al.

(10) Patent No.: US 8,972,201 B2
(45) Date of Patent: Mar. 3, 2015

(54) COMPRESSION OF GENOMIC DATA FILE

(75) Inventors: Sharmila Shekhar Mande, Maharashtra (IN); Monzoorul Hague Mohammed, Andhra Pradesh (IN); Anirban Dutta, Maharashtra (IN); Tungadri Bose, Maharashtra (IN)

(73) Assignee: Tata Consultancy Services Limited, Mumbai (IN)

( * ) Notice: Subject to any disclaimer, the term of this patent is extended or adjusted under 35 U.S.C. 154(b) by 291 days.

(21) Appl. No.: 13/428,794

(22) Filed: Mar. 23, 2012

(65) Prior Publication Data

US 2013/0166518 A1    Jun. 27, 2013

(30) Foreign Application Priority Data

Dec. 24, 2011   (IN) .......................... 3655/MUM/2011

(51) Int. Cl.
   *G06F 19/22*       (2011.01)
(52) U.S. Cl.
   USPC .......................................................... 702/19
(58) Field of Classification Search
   CPC ......... G06F 19/22; G06F 19/18; G06F 19/28; H04L 45/00
   See application file for complete search history.

(56) References Cited

U.S. PATENT DOCUMENTS

| | | | |
|---|---|---|---|
| 7,657,383 B2 * | 2/2010 | Allard et al. | 702/20 |
| 2011/0295858 A1 * | 12/2011 | Ahn et al. | 707/741 |
| 2012/0089339 A1 * | 4/2012 | Ganeshalingam et al. | 702/19 |
| 2012/0233202 A1 * | 9/2012 | Ganeshalingam et al. | 707/769 |
| 2012/0330567 A1 * | 12/2012 | Bauer et al. | 702/20 |
| 2013/0031092 A1 * | 1/2013 | Bhola et al. | 707/737 |
| 2013/0204851 A1 * | 8/2013 | Bhola et al. | 707/693 |

OTHER PUBLICATIONS

Bhloa et al. (2011 IEEE International Conference on Bioinformatics and Biomedicine (BIBM Conference) Nov. 12-15, 2011, Atlanta, GA, USA).*
Brandon et al. (Bioinformatics (2009) vol. 25, No. 14, pp. 1731-1738.*
Fritz et al. (Genome Research (2011) Published online Jan. 18, 2011.*
Giancarlo et al. (Bioinformatics (2009) vol. 25, No. 13:1575-1586).*
Pinho et al. (PLoS One (2010) vol. 6, No. 6:e21588 (1-7).*
Tembe et al. (Bioinformatics (2010) vol. 26, No. 17:2192-2194).*
W Tembe, et al.; G-SQZ: compact encoding of genomic sequence and quality data; Bioinformatics 2010;vol. 26; pp. 2192-2194.
Young Jun Jeon , et al.; SOLiDzipper: A High Speed Encoding Method for the Next-Generation Sequencing Data. Evolutionary bioinformatics online 2011.
Sebastian Deorowicz, et al.; Compression of DNA sequence reads in FASTQ format. Bioinformatics 2011; vol. 27(6): pp. 860-862.
The 1000 Genomes Project Consortium; A map of human genome variation from population-scale sequencing, Nature (2010) 467, 1061-1073.

* cited by examiner

*Primary Examiner* — Lori A Clow
(74) *Attorney, Agent, or Firm* — Barnes & Thornburg LLP

(57) ABSTRACT

Systems and methods for compression of a genomic data file are described herein. In one embodiment, genomic sequences, sequence headers, and quality sequences associated with a plurality of data streams provided in a genomic data file are identified. Each of the genomic sequences includes at least one of primary characters and secondary characters. Further, the secondary characters from each of the genomic sequences may be removed to obtain an intermediate genomic sequence file and a quality score corresponding to the secondary character may be modified in quality sequences to obtain an intermediate quality sequence file. Based on the intermediate genomic sequence file and the intermediate quality sequence file, a modified genomic sequence file and a modified quality sequence file, respectively are generated. A compressed genomic data file is obtained using at least the modified genomic sequence and the modified quality sequence.

18 Claims, 4 Drawing Sheets

COMPRESSION OF GENOMIC DATA FILE

TECHNICAL FIELD

The present subject matter relates, in general, to the field of genomics and, in particular, to compression of a genomic data file.

BACKGROUND

Genome sequencing is a field of active research today. An understanding of the genome variation may enable researchers to fully understand the issues of genetic susceptibility and pharmacogenomics of drug response for all individuals as well as personalized molecular diagnostic tests. For such research or medical purposes, genetic material obtained directly from either a biological or an environmental sample is generally sequenced into a plurality of sequences, called genomic sequences. A facility, such as a research laboratory or a clinic involved in genomic study typically uses high capacity platforms, such as next generation sequencing (NGS) platforms capable of generating large number of genome sequences per year. The genomic sequence thus generated may be further processed and assembled into sets called contigs. Generally, the genomic sequences, or contigs, may be stored for future studies for further analysis. Thus, each year, genomic data, such as the genomic sequence and/or the contigs are generated in huge volumes, in the range of hundreds of terabytes (TB), and stored in the repositories.

Typically the genomic data is either archived in repositories, for example, individual repositories associated with laboratories generating the genomic data or public sequence repositories using various data formats, such as fastq and gff. Storage of such huge volumes of data requires the repositories to have large storage disks having huge volumes of storage capacity. Further, with the advances in the research, the genomic data may also increase, thereby increasing maintenance costs and requirements for additional storage space. Furthermore, since the genomic data may be utilized for future references, the genomic data, for instance, in the fastq format may be archived in compressed form so as to decompress or retrieve the same without any loss of information.

SUMMARY

This summary is provided to introduce concepts related to compression of genomic data files, which are further described below in the detailed description. This summary is not intended to identify essential features of the claimed subject matter nor is it intended for use in determining or limiting the scope of the claimed subject matter.

Method(s) and a system(s) for compression of genomic data file are described herein. In one implementation, the method for compression of genomic data includes identifying genomic sequences, sequence headers, and quality sequences associated with a plurality of data streams provided in a genomic data file. Each of the genomic sequences includes at least one of primary characters and secondary characters. Further, the secondary characters from each of the genomic sequences may be removed to obtain an intermediate genomic sequence file. An intermediate quality sequence file is obtained by modifying, in the quality sequences, a quality score corresponding to the secondary character removed from corresponding genomic sequence. Based on the intermediate genomic sequence file and the intermediate quality sequence file, a modified genomic sequence file and a modified quality sequence file, respectively are generated. Further a compressed genomic data file is obtained using at least the modified genomic sequence and the modified quality sequence.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings for reference to like features and components.

DETAILED DESCRIPTION

Figure 1:
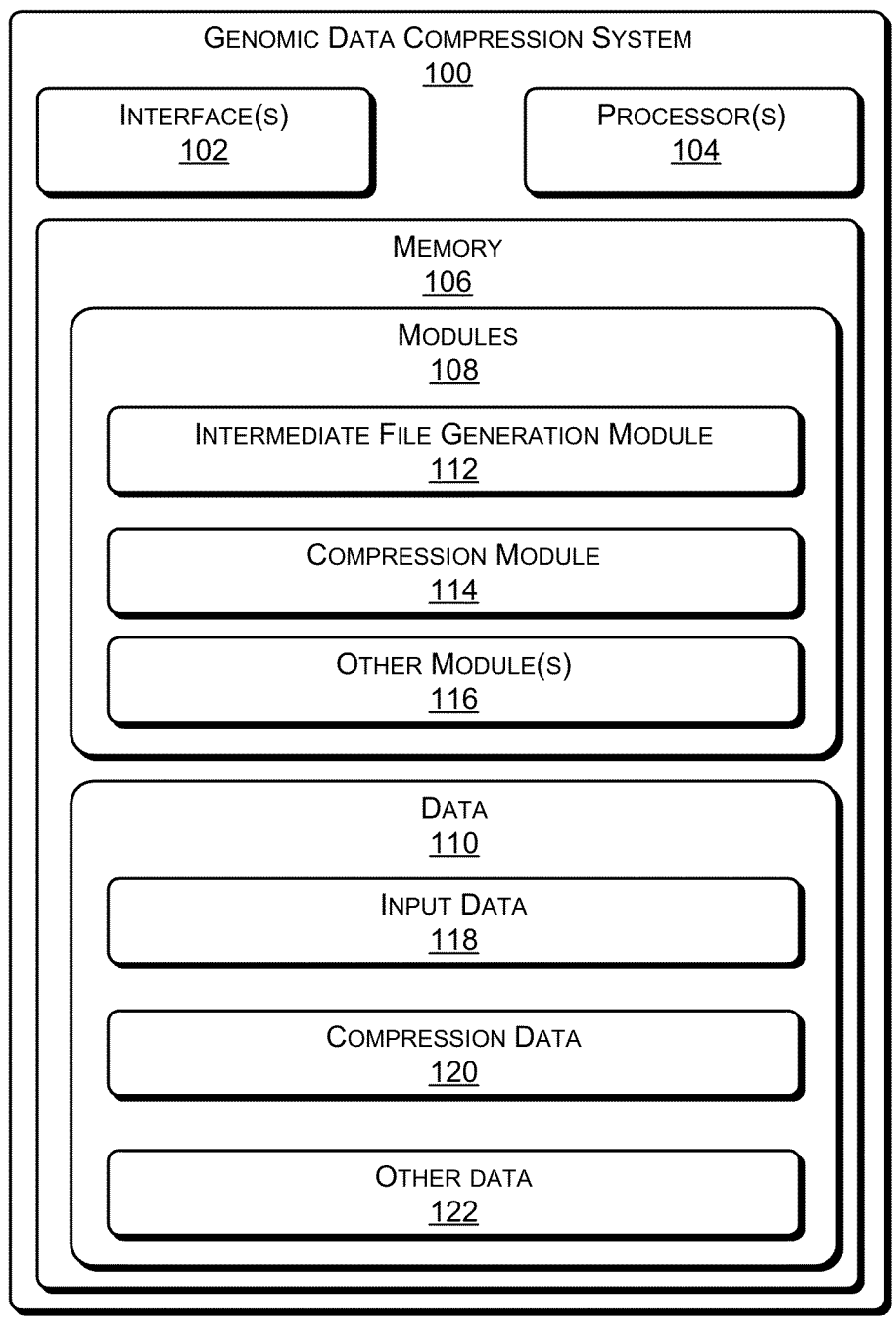
FIG. 1 illustrates a system for compression of a genomic data file, in accordance with an embodiment of the present subject matter.

Systems and methods for compression of genomic data files are described herein. Generally, genetic material extracted directly from either a biological or an environmental sample is processed and stored as genomic data for research or medical purposes. The genomic data typically includes the genetic material sequenced into a plurality of sequences, called genomic sequences. A genomic sequence, as will be known to a person skilled in the art, typically includes data in the form of characters, and is preceded by a header section having information, hereinafter referred to as sequence header, about the genomic sequence. Additionally, for each of the genomic sequences, a corresponding quality sequence is included in quality data, which may be stored along with the genomic data. Further, a quality sequence includes a corresponding quality score for each of the characters in the corresponding genomic sequence. Thus, the quality data may include a plurality of quality sequences, and each of the quality sequences may include a plurality of quality scores.

In order to increase the efficiency of the repositories in storing the genomic data, the quality data and the genomic data may be stored as a genomic data file using a text-based file format, such as a fastq format. Such file formats generally store each of the genomic sequences and their corresponding quality sequences as a single data stream. For example, in fastq format, each data stream typically begins with the sequence header followed by the genomic sequence, a quality header, and the quality sequence corresponding to a genomic sequence.

Further, to facilitate storage of large amount of data and to reduce costs related to the storage of biological databases, the genomic data file may be compressed before being stored. Conventional compression techniques employed by sequence repositories or databases are based on compression techniques that are generally used for compression of text files and are thus unable to optimally compress the genomic data files. Furthermore, certain genomic data compression techniques are configured to compress genomic data files in fastq format. However some of these genomic data compression techniques may not optimally compress the genomic data file, for example, such techniques may not efficiently work for genomic data having genomic sequences of variable read-lengths. Further, few of the implementations of genomic data compression techniques may not be independent of system architecture, i.e., they may be implementable on high bit processors, such as 64 bit processors but not implementable on lower bit processors, such as 32 bit processors.

Additionally, certain compression techniques for genomic data file compression often have high compression and/or decompression time and memory requirements, thus increasing the processing costs. Moreover, an inefficient compression or decompression of the genomic data files in terms of time taken may additionally affect research by hindering quick and efficient storage, retrieval, and transmission of the genomic data.

The present subject matter describes methods and systems for compression of genomic data stored as genomic data files using text-based file format, such as fastq and gff format. Although the description herein is in considerable detail with respect to a fastq format, it will be understood that the methods and systems for compression can be implemented for other file formats as well, albeit with a few variations, as will be understood by a person skilled in the art. According to an embodiment of the present subject matter, a genomic data file having a plurality of data streams is received for compression. Each data stream may include a genomic sequence, an associated sequence header, a quality sequence corresponding to the genomic sequence, and a quality header. For instance, genomic data files in the fastq format normally use four lines per sequence.

The genomic data file may be analyzed to identify the sequence header, the genomic sequence, the quality header, and the quality sequences for all the data streams. The sequence header, the genomic sequence, and the quality sequences for the data streams are subsequently separated and combined to obtain a combined sequence header, a combined genomic sequence, and a combined quality sequence, respectively. Further, each of the combined sequence header, the combined genomic sequence, and the combined quality sequence are processed to obtain one or more modified files, such as a modified header file, a modified genomic sequence file, a modified quality sequence file, an extra characters file, and an attributes file.

In one implementation, the combined genomic sequence and the combined quality sequence are analyzed to identify the primary characters, the secondary characters, and their corresponding quality scores. For instance, in a nucleotide sequence, 'A', 'T', 'G', and 'C', which correspond to four nucleotide bases, adenine (A), thymine (T), guanine (G), and cytosine (C) may be identified as the primary characters, while non-ATGC characters, like 'U', 'Y', 'W', 'M', 'K', 'B', 'V', 'D', 'N', 'X', 'H', 'R', and 'S' may be identified as the secondary characters. The secondary characters may then be removed from the combined genomic sequence to obtain an intermediate genomic sequence file. Further, the quality scores corresponding to the secondary characters may be modified in the combined quality sequence to obtain an intermediate quality sequence file. In one implementation, the quality scores corresponding to the secondary characters may be modified based on a set of predetermined rules. For example, the quality scores for one or more predetermined secondary characters, say 'N' and 'X' may be modified using an ASCII encoding scheme, while the quality scores of the remaining secondary characters, hereinafter referred to as additional characters, may be replaced using a predetermined ASCII value. In another example, all the secondary characters having the quality score above a threshold value may be identified as the additional characters and the quality score of the additional characters may be replaced using the predetermined ASCII value. Identity and quality scores for all the additional characters may be saved in the extra characters file.

The intermediate genomic sequence file may be subsequently encoded to obtain a modified genomic sequence file. For instance, the primary characters may be represented as bits to obtain the modified genomic sequence file in a bit-stream encoded format. Further, the intermediate quality sequence file may be analyzed to determine continuous stretches of similar quality scores. Such continuous stretches may then be replaced by a single instance of the quality score and a run-length value indicating the length of the continuous stretch to obtain the modified quality sequence file.

Further, the combined sequence header may be analyzed to identify identical and non-identical portions between two consecutive sequence headers. In one implementation, the combined header sequence may be delta-encoded based on the identification. Additionally, the sequence headers that do not conform to the standard formats are aligned, for example, using a procedure of global-alignment and their differences are subsequently indexed. Furthermore, length of the genomic sequences having variable length is appended with the corresponding sequence header if it is not already mentioned in the header. The modified header file, thus obtained may be saved along with the modified genomic sequence file and the modified quality sequence file. Further, attributes having information about additional information, such as the standard format of the sequence header and the length of the fixed-length genomic sequences are saved in the attribute file.

The modified header file, the attribute file, modified genomic sequence file, the modified quality sequence file, and the extra characters file may be archived together to generate a final output file, referred to as compressed genomic data file that can be stored for further processing and/or future references. Further, in one embodiment, the modified header file, the attribute file, modified genomic sequence file, the modified quality sequence file, and the extra characters file may be separately compressed using any known method of text-file compression before being archived as the compressed genomic data file.

Due to the compression of data at various stages, the compressed genomic data file thus obtained is not only efficient in terms of compression ratio and compression time but is also lossless in terms of information accuracy. The provision for identification and removal of secondary characters from the genomic sequences ensures reduction of bit allocation for the genomic sequences. For instance, bit-encoding the intermediate genomic sequence file takes less number of bits than would have been required for encoding the genomic sequence. In addition, modifying or replacing the quality scores corresponding to the secondary characters ensures that a lossless decryption of the genomic sequences and the quality sequences can be performed. Further, modifying the quality sequence and the sequence header ensures that number of bits used for encoding the modified quality sequence file and the modified header file are less than number of bits that would have been required for encoding the quality sequence and the sequence header. For instance, run-length encoding the intermediate quality sequence reduces length of the quality sequences.

Although the description herein is with reference to certain sequences, the systems and methods may be implemented for other sequences, such as amino acid sequences, as well, albeit with a few variations, as will be understood by a person skilled in the art.

While aspects of described systems and methods for compression of genomic data files can be implemented in any number of different computing systems, environments, and/or configurations, the embodiments are described in the context of the following exemplary system(s).

FIG. 1 illustrates a genomic data compression system 100, according to an implementation of the present subject matter. The genomic data compression system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the genomic data compression system 100, hereinafter referred to as, the system 100 includes interface(s) 102, one or more processor(s) 104, and a memory 106 coupled to the processor(s) 104.

The interfaces 102 may include a variety of software and hardware interfaces, for example, interfaces for peripheral device(s), such as a keyboard, a mouse, an external memory, and a printer. Further, the interfaces 102 may enable the system 100 to communicate with other devices, such as web servers and external databases. The interfaces 102 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 102 may include one or more ports for connecting a number of computing systems with one another or to another server computer.

The processor(s) 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 also includes module(s) 108 and data 110.

The modules 108, amongst other things, include routines, programs, objects, components, data structures, etc., which perform particular tasks or implement particular abstract data types. The modules 108 further include an intermediate file generation module 112, a compression module 114, and other module(s) 116. The other modules 116 may include programs that supplement applications on the system 100, for example, programs in the operating system. On the other hand, the data 110 serves, amongst other things, as a repository for storing data processed, received, and generated by one or more of the modules 108. The data 110 includes input data 118, compression data 120, and other data 122. The other data 122 includes data generated as a result of the execution of one or more modules in the other modules 116.

In one implementation, the system 100 is associated with a genomic data repository (not shown in the figure). The genomic data repository includes a plurality of genomic data files having genomic sequences generated by a genomic data generation platform, such as an NGS based platform. The genomic data files, as will be understood, are in a text-file format, such as fastq and gff format and are provided to the system 100 for compression. Although the description of the system and the methods herein is in considerable detail with respect to a nucleotide sequence, it will be understood that the methods and systems for compression can be implemented for other genomic sequences, such as RNA sequences, and amino acid sequences as well, albeit with a few variations, as will be understood by a person skilled in the art.

The system 100, in one implementation, receives the genomic data files having a plurality of data streams from the sequence database. In one implementation, the genomic data file includes the genomic data in a text-format, such that each data stream includes at least a genomic sequence and a corresponding quality sequence. For example, in the fastq format, each data stream typically begins with a sequence header followed by a genomic sequence, a quality header, and a quality sequence corresponding to the genomic sequence. The genomic sequence may include a plurality of primary characters representing useful information, such as nucleotide bases and one or more secondary characters. The sequence header includes information, such as an ID of the project for which the nucleotide sequence is generated and sequence ordering. The quality sequence includes a plurality of quality scores such that a particular quality score corresponds to a particular character in the genomic sequence, while the quality header may include information related to the quality sequence, which may be similar to the sequence header. Although the description herein is in considerable detail with respect to the fastq format, it will be understood that the methods and systems for compression can be implemented for other file formats as well, albeit with a few variations, as will be understood by a person skilled in the art. For the purpose of explanation, and not as a limitation, the foregoing description is made with reference to the following example.

For example, the system 100 may receive the following genomic data file having four data streams (SEQ. ID NO.1, SEQ. ID NO.2, SEQ. ID NO.3, and SEQ. ID NO.4, identified below in Data stream 1, Data stream 2, Data stream 3, and Data stream 4, respectively).

```
Data stream 1:
    @SRR013951.815 30PT5AAXX:8:1:14:518 length=76
    AGTTGATCCACCTGAAGAATTAGGANNNNNNANNTNNGNCACNCNNNNNNNGNNAN
    ANNNNNNNNNCTATAAACCA
    +
    IIIIIIIIIIIIIIHDIII0C1.!!!!!!D!!;!!-!6&>!&!!!!!!!-!!&!'!!!!!!!!!#'-*G5E+'+
Data stream 2:
    @SRR013951.816 30PT5AAXX:8:1:14:399 length=76
    GGGTATGTTCTGTTCTCCTGGCCATNNNNNNANNCNNGNCTTNCNNNNNNNGNNTN
    ANNNNNNNNNTGTCACTGTC
    +
    1II0II2@ICI8=B55C6I441+%:!!!!!!2!!2!!)!%/3!)!!!!!!1!!&!-!!!!!!!!))'#&'-#''''
```

-continued

```
Data stream 3:
  @SRR013951.817 30PT5AAXX:8:1:14:616 length=76
  TGCCTTCAGCCCAAAAAGCCCACGCNNNNNNNANNTNNCNCCTNTNNNNNNNTNNCN
  CNNTNNNNNNTAACTCTCCA
  +
  *&)#+)#(*+#('$$+&&+%$$$#'!!!!!!)!!%!!&!$%#!#!!!!!!!%!!%!&!!$!!!!!!$$$$#%$$&%
Data stream 4:
  @SRR013951.818 30PT5AAXX:8:1:15:558 length=76
  CTGCGCTCCCTCCCTCCACCCACTTNNNNNNCNNCNNTNACTNTNNNNNNNCTNCN
  CNCCNNNNNNCTATTCCCCA
  +
  I0D+5I>><I*'%BIB/II2%+%='!!!!!!I!!5!!-!&+/!#!!!!!!!#%!%!+!%6!!!!!!I#$$#%/&=0
```

In the above example, a first line of each of the data stream represents the sequence header corresponding to the data stream and begins with a '@' character followed by a sequence identifier and an optional description. A second line represents the genomic sequence having primary characters 'A', 'T', 'G', and 'C', known as nucleotide bases, and secondary characters, such as 'N' and 'X'. A third line represents the quality header and includes the symbol '+'. A fourth line represents the quality sequence and includes quality scores corresponding to each of the characters included in the genomic sequence and, therefore, contains the same number of symbols as the characters in the genomic sequence. Further, in one implementation, the quality scores may be encoded and presented as ASCII codes. For instance, in the above example, quality score corresponding to the first character 'T' of the third genomic sequence is represented as '*'. The ASCII encoding may be understood as a scheme to represent a phred score generated by a genomic data generation platform using ASCII codes. In one implementation, the ASCII encoding may vary based on the genomic data generation platform used for generation of the genomic data, as illustrated in table 1.

TABLE 1

| Genomic data generation platform | Quality value/Phred scores (q) | Quality scores (Q) saved in fastq format | ASCII character-set used |
|---|---|---|---|
| Sanger/Roche 454/ SOLiD | 0-93 | quality + 33 | 33-126 |
| Illumina/Solexa | 0-62 | quality + 64 | 64-126 |

As illustrated in table 1, for genomic data generated using Sanger or Roche 454, or SOLiD platforms, a value of 33 is added to the Phred score to obtain the ASCII encoded quality score. For the genomic data generated using Illumina or Solexa platforms, a value of 64 is added to the Phred score to obtain the ASCII encoded quality score.

The genomic data file thus received may be saved in the input data 118. In one implementation, the sequence headers, the genomic sequences, the quality headers, and the quality sequences, corresponding to the data streams are identified and separated for further processing. For the purpose, the intermediate file generation module 112 accesses the input data 118 to obtain the genomic data file. The intermediate file generation module 112 analyzes the genomic data file to identify the sequence headers, the genomic sequences, the quality headers, and the quality sequences, corresponding to all the data streams. In one implementation, the intermediate file generation module 112 may identify the sequence headers based on one or more preconfigured parameters or rules. For instance, the intermediate file generation module 112 may be configured to identify the information between the symbol '@' and the first character of the genomic sequence as the sequence header. Subsequently, the intermediate file generation module 112 may combine the sequence headers corresponding to all the data streams to obtain a combined sequence header.

For instance, in the previous example of the genomic data received by the system 100, the intermediate file generation module 112 may combine all the sequence headers to provide the combined sequence header as follows:
  @SRR013951.815 30PT5AAXX:8:1:14:518 length=76
  @SRR013951.816 30PT5AAXX:8:1:14:399 length=76
  @SRR013951.817 30PT5AAXX:8:1:14:616 length=76
  @SRR013951.818 30PT5AAXX:8:1:15:558 length=76

For the sake of clarity, the sequence header corresponding to each of the data streams has been indicated as separate entries, it will be understood that the sequence headers of the data streams may be combined together as a single sentence or an entry. The intermediate file generation module 112 may subsequently save the combined sequence header in the compression data 120.

Further, the intermediate file generation module 112 may determine the genomic sequences from the genomic data file. In one implementation, the intermediate file generation module 112 may identify the information between the sequence header and the symbol '+' as a genomic sequence. On identification of the genomic sequences, the intermediate file generation module 112 combines the genomic sequences to obtain the combined genomic sequence.

Referring to the example discussed above, the intermediate file generation module 112 may combine all the genomic sequences to provide the combined genomic sequence as follows (SEQ. ID NO.5):

AGTTGATCCACCTGAAGAATTAGGANNNNNNANNTNNGNCACNCNNNNN

NNGNNANANNNNNNNNNCTATAAACCAGGGTATGTTCTGTTCTCCTGGC

CATNNNNNNANNCNNGNCTTNCNNNNNNNGNNTNANNNNNNNNNTGTCA

CTGTCTGCCTTCAGCCCAAAAAGCCCACGCNNNNNNANNTNNCNCCTNT

NNNNNNNTNNCNCNNTNNNNNNTAACTCTCCACTGCGCTCCCTCCCTCC

ACCCACTTNNNNNNCNNCNNTNACTNTNNNNNNNCTNCNCNCCNNNNNN

CTATTCCCCA

The combined genomic sequence, thus obtained, may be saved in the compression data 120. The intermediate file generation module 112 identifies all the quality sequences from the genomic data file. The intermediate file generation module 112 may identify all the information after the quality header, the symbol '+' in the above example, as a quality sequence. On identification of all the quality sequences, the intermediate file generation module 112 may combine the quality sequences to obtain the combined quality sequence.

For instance, in the previous example of the genomic data file, the intermediate file generation module 112 may combine the genomic sequences to obtain the combined quality sequence as follows:

```
IIIIIIIIIIIIIIIHDIII0C1.!!!!!!D!!;!!−!6&>!&!!!!!!!−!!&!'!!!!!!!!!#,−
*G5E+'+1II0II2@ICI8=B55C6I441+%:!!!!!!2!!2!!)!%/3!)!!!!!!!!1!!&!−
!!!!!!!!))'#&'*#""*&)#+)#(*+#('$$+&&+%$$$#'!!!!!!)!!%!!&!$%#!#!!!!!!!%!!%!&!!$!!!
!!!$$$$#%$$&%I0D+5I>><I*'%BIB/II2%+%='!!!!!!I!!5!!−
!&+/!#!!!!!!#%!%!+!%6!!!!!!I#$$#%/&=0
```

The combined quality sequence, thus obtained, may be saved in the compression data 120. In an example, the quality header may not be considered for the compression of the genomic data file, since the quality header typically includes either only the symbol '+' or the same information as the sequence header.

The combined sequence header, the combined genomic sequences, and the combined quality sequences may be further processed for compressing the genomic data file. In one implementation, the intermediate file generation module 112 analyzes the combined genomic sequence to determine the type of character coding used to represent the data in the combined genomic sequence. For instance, the intermediate file generation module 112 may determine whether the data has been represented using a 'base-space coding' or a 'color-space coding'. The base-space coding, as will be understood, uses standard International Union of Pure and Applied Chemintermediate file generation module 112 may save an attribute defining the type of character coding in an attribute file. Referring to the previous example, the attribute file may indicate that 'A' corresponds to '1', 'T' corresponds to 2, and so on. The attribute file may be saved in the compression data 120.

Further, the intermediate file generation module 112 analyzes the combined genomic sequence to identify the primary characters and the secondary characters. For instance, in a nucleotide sequence, the intermediate file generation module 112 may identify the characters 'A', 'T', 'G', and 'C', as the primary characters, and non-ATGC characters, like 'U', 'Y', 'W', 'M', 'K', 'B', 'V', 'D', 'N', 'X', 'H', 'R', and 'S as the secondary characters. Further, the intermediate file generation module 112 may analyze the combined quality sequences and based on positions of the secondary characters in the combined genomic sequence, identifies and modifies quality scores corresponding to the secondary characters.

In one embodiment, the intermediate file generation module 112 modifies the quality scores corresponding to the secondary characters based on a set of predetermined rules as illustrated in table 2.

TABLE 2

| Characters in the genomic sequence | Quality scores (q) in the quality sequence | ASCII encoded quality scores (Q0) in the quality sequence | Characters in the intermediate genomic sequence | ASCII encoded quality scores (Q1) in the intermediate quality sequence | Extra characters file (EI) | Range of ASCII characters used |
|---|---|---|---|---|---|---|
| A | q | q + 33 | A | q + 33 | left blank | 33-126 |
|   |   | q + 64 |   | q + 64 |   | 64-126 |
| T | q | q + 33 | T | q + 33 |   | 33-126 |
|   |   | q + 64 |   | q + 64 |   | 64-126 |
| G | q | q + 33 | G | q + 33 |   | 33-126 |
|   |   | q + 64 |   | q + 64 |   | 64-126 |
| C | q | q + 33 | C | q + 33 |   | 33-126 |
|   |   | q + 64 |   | q + 64 |   | 64-126 |
| N | $0 \leq q < 20$ | q + 33 | removed from stream | q + 130 |   | 130-149 |
|   |   | q + 64 |   | q + 150 |   | 150-169 |
| X | $0 \leq q < 20$ | q + 33 | removed from stream | q + 170 |   | 170-189 |
|   |   | q + 64 |   | q + 190 |   | 190-209 |
| N/X | $q \geq 20$ | q + 33 | removed from stream | 210 | <character><q + 33> <character><q + 64> | 210 |
|   |   | q + 64 |   |   |   |   |
| Additional character | q | q + 33 | removed from stream |   | <character><q + 33> <character><q + 64> |   |
|   |   | q + 64 |   |   |   |   | istry (IUPAC) characters, such as 'A', 'T', 'G', and 'C' to represent the data. The color-space coding, uses non-IUPAC characters, such as numerals 0, 1, 2, 3, and 4. In case, the character coding used is a color-space coding, the intermediate file generation module 112 converts the characters of the combined genomic sequence to base-space coding to provide a pseudo base-space file representation. For example, the intermediate file generation module 112 may convert the character '0' to the character 'A', '1' to 'T', '2' to 'G', '3' to 'C', '4' to 'N' and '.' to 'X'. The intermediate file generation module 112 may save the base-space file representation and use the same as combined genomic sequence for the purpose of the compression of the genomic data file. Additionally, the In one implementation, the intermediate file generation module 112 may be configured to modify the quality scores for one or more predetermined secondary characters, say 'N' and 'X' using an encoding scheme, such as ASCII encoding. While the quality scores of the remaining secondary characters, hereinafter referred to as additional characters, may be replaced using a predetermined value, such as an ASCII value. Further, in an example, the intermediate file generation module 112 may identify the secondary characters having the quality score above a threshold value, as the additional characters and replace their associated quality scores using the predetermined ASCII value. For example, as illustrated in table 2, for the secondary characters 'N' and 'X' if the Phred score, i.e., a non-ASCII encoded quality score (q) is greater than 20, the intermediate file generation module 112 may identify the secondary character as an additional character and replace the corresponding quality score in the combined quality sequence using a predetermined value 210. On the other hand, if the non-ASCII encoded quality score, q, for the secondary characters 'N' and 'X' is between 0 and 20, the intermediate file generation module 112 may ASCII encode the quality score based on the genomic data generation platform used. For instance, if the genomic data is generated using Illumina or Solexa platforms, the intermediate file generation module 112 may add a value of 150 to the non-ASCII encoded quality score corresponding to 'N' to obtain the ASCII encoded quality score (Q1).

The intermediate file generation module 112 may thus modify the quality scores of all the secondary characters to obtain an intermediate quality sequence file. Further, the intermediate file generation module 112 may remove all the secondary characters from the combined genomic sequence to generate an intermediate genomic sequence file having the primary characters. Additionally, the intermediate file generation module 112 may save identity and quality scores for all the additional characters in the extra characters file using a format as shown in the table 2.

For instance, in the previous example of the genomic data file, the intermediate file generation module 112 removes all the secondary characters to obtain the intermediate genomic sequence file as follows (SEQ. ID NO.6):

AGTTGATCCACCTGAAGAATTAGGAATGCACCGAACTATAAACCAGGGT

ATGTTCTGTTCTCCTGGCCATACGCTTCGTATGTCACTGTCTGCCTTCA

GCCCAAAAAGCCCACGCATCCCTTTCCTTAACTCTCCACTGCGCTCCCT

CCCTCCACCCACTTCCTACTTCTCCCCCTATTCCCCA

Further, in the previous example of the genomic data file, the intermediate file generation module 112 modifies the quality scores to obtain the intermediate quality sequence file as follows:

file and intermediary quality file are independent of each other, these two files may be generated in any order.

The intermediate genomic sequence file having just the primary characters and the intermediate quality sequence file may be subsequently encoded to obtain a modified genomic sequence file and a modified quality sequence file. In one implementation, the compression module 114 accesses the compression data 120 to obtain the intermediate genomic sequence file.

The compression module 114 may be configured to encode the intermediate genomic sequence file using, for example, a bit-stream encoding scheme to obtain the modified genomic sequence file in a bit-stream encoded format. In one implementation, compression module 114 may represent each of the primary characters as bits to obtain the modified genomic sequence file. For example, the compression module 114 may represent the character 'A' as 00, 'T' as 01, 'G' as 10, and 'C' as 11. The modified genomic sequence file may be saved by the compression module 114 in the compression data 120.

Further, the compression module 114 may be configured to encode the intermediate quality sequence file using, for example, a run-length encoding scheme to obtain the modified quality sequence file in a run-length encoded format. The run-length encoding may be understood as an encoding scheme in which stretches of a similar value are replaced by a single instance of the value followed by a length of the stretch. In one implementation, the compression module 114 analyzes the intermediate quality sequence file to identify instances where a particular quality score is followed by the same quality score. Based on the identification, the compression module 114 determines, for all the instances, a run-length, i.e., the number of times the particular quality score value has been repeated in the instance. The instances having run-length of more than a predetermined value may be identified by the compression module 114 as continuous stretches of similar quality scores. In an example, the instances having run-length of more than 4 times may be identified by the compression module 114 as stretches of continuous values. The compression module 114 subsequently replaces the iden-

---

(49)(49)(49)(49)(49)(49)(49)(49)(49)(49)(49)(49)(49)(49)(49)(49)(48)(44)(49)(49)(49)(30)(43)(31)(2e)(a3)(a3)(a3)(a3)(a3)(a3)(44)(a3)(a3)(3b)(a3)(a3)(2d)(a3)(36)(26)(3e)(a3)(26)(a3)(a3)(a3)(a3)(a3)(a3)(a3)(2d)(a3)(a3)(26)(a3)(27)(a3)(a3)(a3)(a3)(a3)(a3)(a3)(a3)(23)(2c)(2d)(2a)(47)(35)(45)(2b)(27)(2b)(31)(49)(49)(30)(49)(49)(32)(40)(49)(43)(49)(38)(3d)(42)(35)(35)(43)(36)(49)(34)(34)(31)(2b)(25)(3a)(a3)(a3)(a3)(a3)(a3)(a3)(32)(a3)(32)(a3)(a3)(29)(a3)(25)(2f)(33)(a3)(29)(a3)(a3)(a3)(a3)(a3)(a3)(31)(a3)(a3)(26)(a3)(2d)(a3)(a3)(a3)(a3)(a3)(a3)(a3)(a3)(29)(29)(27)(23)(26)(27)(2a)(23)(22)(22)(2a)(26)(29)(23)(2b)(29)(23)(28)(2a)(2b)(23)(28)(27)(24)(24)(2b)(26)(26)(2b)(25)(24)(24)(24)(23)(27)(a3)(a3)(a3)(a3)(a3)(a3)(29)(a3)(a3)(25)(a3)(a3)(26)(a3)(24)(25)(23)(a3)(23)(a3)(a3)(a3)(a3)(a3)(a3)(a3)(a3)(25)(a3)(25)(a3)(26)(a3)(a3)(24)(a3)(a3)(a3)(a3)(a3)(a3)(24)(24)(24)(24)(23)(25)(24)(24)(26)(25)(49)(30)(44)(2b)(35)(49)(3e)(3e)(3c)(49)(2a)(27)(25)(42)(49)(42)(2f)(49)(49)(32)(25)(2b)(25)(3d)(27)(a3)(a3)(a3)(a3)(a3)(a3)(49)(a3)(a3)(35)(a3)(a3)(2d)(a3)(26)(2b)(2f)(a3)(23)(a3)(a3)(a3)(a3)(a3)(a3)(a3)(23)(25)(a3)(25)(a3)(2b)(a3)(25)(36)(a3)(a3)(a3)(a3)(a3)(49)(23)(24)(24) (23)(25)(2f)(26)(3d)(30)

---

It will be understood that as the intermediate quality sequence file may include various non-printable ASCII characters, therefore for the sake of clarity the quality scores have been represented here using hexadecimal codes.

Further, since in the above example, there are no additional characters, the extra characters file may be a blank file. Additionally, since the generation of the intermediary sequence tified stretches with a single instance of the particular quality score followed by the associated run-length to obtain the modified quality sequence file.

For instance, in the previous example of the genomic data file, the compression module 114 identifies all the stretches of quality scores having run-length of more than 4, in bold script, as follows:

---

(49)(49)(49)(49)(49)(49)(49)(49)(49)(49)(49)(49)(49)(49)(49)(49)(48)(44)(49)(49)(49)(30)(43)(31)(2e)(a3)(a3)(a3)(a3)(a3)(a3)(44)(a3)(a3)(3b)(a3)(a3)(2d)(a3)(36)(26)(3e)(a3)(26)(a3)(a3)(a3)(a3)(a3)(a3)(2d)(a3)(a3)(26)(a3)(27)(a3)(a3)(a3)(a3)(a3)(a3)(a3)(a3)(23)(2c)(2d)(2a)(47)(35)(45)(2b)(27)(2b)(31)(49)(49)(3

-continued

```
0)(49)(49)(32)(40)(49)(43)(49)(38)(3d)(42)(35)(35)(43)(36)(49)(34)(34)(31)(2b)(25)(3a)(a3)(a3)(a3)
(a3)(a3)
(a3)(32)(a3)(a3)(32)(a3)(a3)(29)(a3)(25)(2f)(33)(a3)(29)(a3)(a3)(a3)(a3)(a3)(a3)(a3)(31)(a3)(a3)(26)(a3)
(2d)(a3)(a3)(a3)(a3)(a3)(a3)(a3)(a3)(29)(29)(27)(23)(26)(27)(2a)(23)(22)(22)(2a)(26)(29)(23)
(2b)(29)(2
3)(28)(2a)(2b)(23)(28)(27)(24)(24)(2b)(26)(26)(2b)(25)(24)(24)(24)(23)(27)(a3)(a3)(a3)(a3)(a3)(a3)
(29)(a3)
(a3)(25)(a3)(a3)(26)(a3)(24)(25)(23)(a3)(23)(a3)(a3)(a3)(a3)(a3)(a3)(a3)(25)(a3)(a3)(25)(a3)(26)(a3)(a3)
(24)(a3)(a3)(a3)(a3)(a3)(a3)(24)(24)(24)(24)(23)(25)(24)(24)(26)(25)(49)(30)(44)(2b)(35)(49)(3e)(3e)(3c)(4
9)(2a)(27)(25)(42)(49)(42)(2f)(49)(49)(32)(25)(2b)(25)(3d)(27)(a3)(a3)(a3)(a3)(a3)(a3)(49)(a3)(a3)(35)(a3)
(a3)(2d)(a3)(26)(2b)(2f)(a3)(23)(a3)(a3)(a3)(a3)(a3)(a3)(a3)(23)(25)(a3)(25)(a3)(2b)(a3)(25)(36)(a3)(a3)(a
3)(a3)(a3)(a3)(49)(23)(24)(24) (23)(25)(2f)(26)(3d)(30)
```

The compression module 114 subsequently removes all the identified stretches from the intermediate quality sequence to obtain the modified quality sequence file as follows:

```
(49)16(48)(44)(49)(49)(49)(30)(43)(31)(2e)(a3)6(44)(a3)(a3)(3b)(a3)(a3)(2d)(a3)(36)(26)(3e)(a3)(26)(a3)7
(2d)(a3)(a3)(26)(a3)(27)(a3)9(23)(2c)(2d)(2a)(47)(35)(45)(2b)(27)(2b)(31)(49)(49)(30)(49)(49)(32)(40)(49)
(43)(49)(38)(3d)(42)(35)(35)(43)(36)(49)(34)(34)(31)(2b)(25)(3a)(a3)6(32)(a3)(a3)(32)(a3)(a3)(29)(a3)(25)
(2f)(33)(a3)(29)(a3)7(31)(a3)(a3)(26)(a3)(2d)(a3)9(29)(29)(27)(23)(26)(27)(2a)(23)(22)(22)(2a)(26)(29)(23)
(2b)(29)(23)(28)(2a)(2b)(23)(28)(27)(24)(24)(2b)(26)(26)(2b)(25)(24)(24)(24)(23)(27)(a3)6(29)(a3)(a3)(25)
(a3)(a3)(26)(a3)(24)(25)(23)(a3)(23)(a3)7(25)(a3)(a3)(25)(a3)(26)(a3)(a3)(24)(a3)6(24)(24)(24)(23)(25)
(24)(24)(26)(25)(49)(30)(44)(2b)(35)(49)(3e)(3e)(3c)(49)(2a)(27)(25)(42)(49)(42)(2f)(49)(49)(32)(25)(2b)(2
5)(3d)(27)(a3)6(49)(a3)(a3)(35)(a3)(a3)(2d)(a3)(26)(2b)(2f)(a3)(23)(a3)7(23)(25)(a3)(25)(a3)(2b)(a3)(25)(3
6)(a3)6(c3)(49)(23)(24)(24) (23)(25)(2f)(26)(3d)(30)
```

The modified quality sequence file may be stored in the compression data 120. The compression module 114 may further modify the combined sequence header to obtain the modified header file. In one implementation, the compression module 114 may analyze the combined sequence header to identify, for each of the sequence header, various sections, such as a sequence identifier and sequencing experiment details corresponding to the sequence header. A sequence identifier may be defined as a part of a sequence header that may be used to identify the genomic sequence. The sequencing experiment details may be understood as a part of a sequence header that provides details about the experiment for which the associated genomic data has been generated. Additionally, if the sequence headers also include the length of their corresponding genomic sequences, the compression module 114 may also identify the length for all the sequence headers from the combined sequence header. For instance, in the above example of genomic data file, for a particular sequence header, the sequence identifier may be identified as '@SRR013951.815', the sequencing experiment details may be identified as '30PT5AAXX:8:1:14:518', a part having the length may be identified as 'length=76'. Further, the compression module 114 may analyze the various sections for all the sequence headers, and determine, for the various sections, all the identical and non-identical portions between two consecutive sequence headers. For example, the compression module 114 may also analyze all the sequence identifiers and determine identical and non-identical portions between the sequence identifiers of all the sequence headers.

The compression module 114 may, in one implementation, save the non-identical portions in a delta-encoded format. For instance, in the previous example, the compression module 114 may determine that in all the sequence identifiers the portion '@SRR013951.' is identical, whereas '815', '816', '817', and '818' are the non-identical portions. The compression module 114 may index identical portions for the various sections of all the sequence headers. Further, if the non-identical portions follow a consistent increasing or decreasing numerical pattern, the compression module 114 may delta-encode the various sections based on the index and the non-identical portions to obtain the modified header file. The modified header file thus obtained includes the index and the delta-encoded non-identical portions. Additionally, if length information for genomic sequences having variable length is not provided in the sequence header, the compression module 114 determines the length and appends it with the corresponding sequence header. Additionally, for the sequence headers that do not conform to a standard format of sequence header representation, the compression module 114 may be configured to align the sequence headers. For example, the compression module 114 may align the sequence headers using a procedure of global-alignment and subsequently index their differences to obtain the modified header file.

For instance, in the previous example of the genomic data file, the compression module 114 modifies the combined sequence header to obtain the modified header file as follows:

```
<header_stream_part_1>
(96)815(96)1(96)1(96)1
</header_stream_part_1>
<header_stream_part_2>
(97)(99)399(99)616(9a)5:558
</header_stream_part_2>
<header_stream_part_3>
(98)
</header_stream_part_3>
<index>
@SRR013951.                (96)
30PT5AAXX:8:1:14:518       (97)
length=76                  (98)
30PT5AAXX:8:1:14:          (99)
30PT5AAXX:8:1:1            (9a)
</index>
```

The modified header file, thus obtained may be saved in the compression data 120. Further, the compression module 114 saves attributes having information about additional information, such as whether the sequence headers follow the standard format and whether the genomic sequences are of variable lengths, which are saved in the attribute file.

The modified header file, the modified genomic sequence file, the modified quality sequence file, the extra characters file, and the attribute file archived together thus provide the compressed genomic data file and may be used for further processing or storage. Further, in order to facilitate an efficient processing and storing, the compression module 114 may further-compress all the files individually using any suitable compression technology and archive the files together to generate a final output file, referred to as the compressed genomic data file. As will be understood by a person skilled in the art, the compression module 114 may use any known archiving or compression technology, for example, the modified genomic sequence file may be further-compressed using LZMA compression technique. While, the modified header file, the modified quality sequence file, the extra characters file, and the attribute file may be further-compressed using PPMD compression technique.

Validation and Results

For the purpose of validation, 11 genomic data files, in fastq format, were downloaded from the online repository of the 1000 genomes project present in the NCBI database and compressed using the system 100 in accordance with the present embodiment. The results were further compared with conventional techniques, such as GZIP—version 1.4, and LZMA—version 9.20, and DSRC (DNA Sequence Reads Compression technique). The experiments were performed using a desktop having a 2.33 gigahertz (Ghz) dual core processor with 2 gigabytes (GB) RAM. The system 100 and the other compression techniques were used to compress the 11 genomic data files and their results were evaluated using the compression ratio achieved by all the techniques and the time taken for compression and decompression. In one implementation, the compression ratio may be understood as a percentage ratio of the compressed file size and the size of the original genomic data file.

Results obtained after compression of the various genomic data files using the system 100 and the conventional techniques are summarized in table 3.

Further, the compression ratios corresponding to each of the compression technique are indicated in parenthesis.

The compression ratios obtained using the system 100 and the conventional techniques may be compared to obtain a percentage improvement in compression ratio over conventional techniques for each genomic data file. The percentage improvement may be understood as a percentage gain in the compression ratio achieved using the system 100 over the compression ratio achieved using the conventional techniques. Further, the compression ratios achieved for genomic data files generated using different genomic data generation platforms may also be compared for the percentage improvement. Percentage improvements with respect to the results obtained using the conventional techniques are depicted in table 4.

TABLE 4

| Genomic data files | Percentage improvement in compression ratio achieved using the present system | | | |
|---|---|---|---|---|
| | gzip-default | gzip-9 | lzma (7zip) | DSRC |
| SRR001471 | 37.15 | 35.34 | 20.26 | 11.26 |
| SRR003177 | 35.89 | 34.01 | 20.07 | 11.61 |
| SRR003186 | 34.91 | 33.24 | 19.09 | 9.89 |
| Average for Roche-454 | 35.99 | 34.2 | 19.81 | 10.92 |
| SRR007215_1 | 38.82 | 36.92 | 28.92 | 1.88 |
| SRR010637 | 35.03 | 33.27 | 25.53 | 1.67 |
| SRR070253 | 33.98 | 32.41 | 22.78 | 6.57 |
| Average for SOLiD | 35.94 | 34.2 | 25.74 | 3.37 |
| SRR032638 | 37.41 | 35.87 | 24.02 | 9.28 |
| SRR013951_2 | 31.03 | 29.73 | 16.3 | 5.67 |
| SRR027520_1 | 34.34 | 32.79 | 19.36 | 6.99 |
| SRR027520_2 | 34.38 | 33.02 | 19.51 | 7.01 |
| SRR099458 | 38.02 | 36.87 | 23.39 | 13.32 |
| Average for Illumina | 35.04 | 33.66 | 20.52 | 8.46 |
| Average for all genomic data files | 35.54 | 33.95 | 21.75 | 7.74 |

TABLE 3

| Genomic data files | Genomic data generation platforms | Size of original genomic data files (in megabytes) | Size of compressed genomic data files (in megabytes). Compression ratio* is indicated in brackets | | | | |
|---|---|---|---|---|---|---|---|
| | | | FQC | gzip - default | gzip -9 | lzma (7zip) | DSRC |
| SRR001471 | Roche-454 | 206 | 41 (19.9) | 66 (32) | 64 (31.1) | 52 (25.2) | 46 (22.3) |
| SRR003177 | Roche-454 | 1141 | 238 (20.9) | 371 (32.5) | 360 (31.6) | 297 (26) | 269 (23.6) |
| SRR003186 | Roche-454 | 845 | 190 (22.5) | 291 (34.4) | 284 (33.6) | 234 (27.7) | 210 (24.9) |
| SRR007215_1 | SOLiD | 663 | 100 (15.1) | 163 (24.6) | 158 (23.8) | 141 (21.3) | 102 (15.4) |
| SRR010637 | SOLiD | 1990 | 382 (19.2) | 587 (29.5) | 572 (28.7) | 512 (25.7) | 388 (19.5) |
| SRR070253 | SOLiD | 41086 | 8328 (20.3) | 12614 (30.7) | 12321 (30) | 10786 (26.3) | 8914 (21.7) |
| SRR032638 | Illumina (Solexa) | 45 | 8 (17.8) | 13 (28.9) | 13 (28.9) | 11 (24.4) | 9 (20) |
| SRR013951_2 | Illumina (Solexa) | 3043 | 889 (29.2) | 1289 (42.4) | 1265 (41.6) | 1062 (34.9) | 942 (31) |
| SRR027520_1 | Illumina (Solexa) | 4586 | 1071 (23.4) | 1631 (35.6) | 1593 (34.7) | 1328 (29) | 1151 (25.1) |
| SRR027520_2 | Illumina (Solexa) | 4586 | 1094 (23.9) | 1667 (36.3) | 1633 (35.6) | 1359 (29.6) | 1177 (25.7) |
| SRR099458 | Illumina (Solexa) | 24714 | 5019 (20.3) | 8099 (32.8) | 7950 (32.2) | 6552 (26.5) | 5791 (23.4) |
| Average compression ratio* for all data sets | | | 21.14 | 32.7 | 31.98 | 26.96 | 22.96 |

Table 3 indicates size, in megabytes (MB), of the final compressed genomic data files for the various techniques.

As can be seen from the tables 3 and 4, the system 100 is approximately 8% to 35% efficient as compared to the conventional techniques in terms of the compression ratio achieved. Further, it may also be observed that the compression ratios achieved by the system 100 significantly improves for data files generated using certain genomic data generation platforms. For instance, in the case of data sets generated using Roche-454 and Illumina sequencing platforms, the system 100 provides approximately 11% and 8.5% improvement in compression ratio over that obtained using DNA Sequence Reads Compression (DSRC) technique.

Further, the results of compression and decompression time using the system 100 and the conventional techniques are depicted in table 5.

TABLE 5

| Genomic data files | Size of Genomic data files (in megabytes) | Compression Time (CT) and Decompression time (DT) in seconds | | | | | | | | |
|---|---|---|---|---|---|---|---|---|---|---|
| | | system 100 | | gzip-default | | gzip -9 | | lzma (7zip) | | DSRC | |
| | | CT | DT | CT | DT | CT | DT | CT | DT | CT | DT |
| SRR001471 | 206 | 21 | 17 | 44 | 4 | 128 | 5 | 279 | 7 | 6 | 7 |
| SRR003177 | 1141 | 170 | 131 | 264 | 23 | 1233 | 24 | 1621 | 42 | 29 | 40 |
| SRR003186 | 845 | 114 | 94 | 203 | 18 | 551 | 19 | 1270 | 32 | 23 | 31 |
| SRR007215_1 | 663 | 77 | 63 | 55 | 12 | 89 | 12 | 442 | 27 | 32 | 22 |
| SRR010637 | 1990 | 236 | 181 | 215 | 36 | 338 | 36 | 1653 | 27 | 86 | 73 |
| SRR070253 | 41086 | 5272 | 4199 | 5273 | 774 | 8851 | 818 | 36296 | 1782 | 1905 | 1595 |
| SRR032638 | 45 | 5 | 4 | 8 | 1 | 17 | 1 | 54 | 2 | 2 | 2 |
| SRR013951_2 | 3043 | 466 | 367 | 594 | 59 | 994 | 61 | 4006 | 147 | 104 | 131 |
| SRR027520_1 | 4586 | 622 | 511 | 922 | 92 | 1567 | 96 | 5792 | 209 | 152 | 164 |
| SRR027520_2 | 4586 | 617 | 476 | 932 | 92 | 1558 | 97 | 6039 | 205 | 154 | 173 |
| SRR099458 | 24714 | 3595 | 2822 | 5031 | 507 | 10173 | 501 | 34040 | 1040 | 881 | 876 |
| Average processing speed (megabytes/second) | | system 100 | | gzip-default | | gzip -9 | | lzma (7zip) | | DSRC | |
| Compression | | 7.41 | | 6.12 | | 3.25 | | 0.91 | | 24.57 | |
| Decompression | | 9.35 | | 51.24 | | 49.64 | | 23.55 | | 26.62 | |

Table 5 indicates time taken, in seconds, for compression and decompression of the genomic data files using the various techniques. Further, average processing speed, in MB per second, for compression and decompression is independently indicated in the table for the various techniques.

As can be seen from the table 5, the compression time achieved using the system 100 is significantly less than the GZIP (default), the GZIP (-9 option), and the LZMA techniques. For instance, the system 100 is observed to be 8 times faster than the LZMA techniques, 1.2 times faster than the GZIP (default), and 2.3 faster than GZIP (-9 option). The compression time achieved using the system 100 is, however slightly more than the DSRC technique. Further, total time taken for compression and decompression using the system 100 is significantly less than the GZIP (-9 option), and the LZMA techniques. The total time taken for compression and decompression using the system 100 is comparable with the GZIP (default) and slightly more than the DSRC technique. Although the time taken by the system 100 for compression and decompression is slightly more than the time taken by the DSRC technique, the gains in compression ratio achieved by the system 100 is significantly better than the DSRC technique as can be seen in the table 4.

Figure 2:
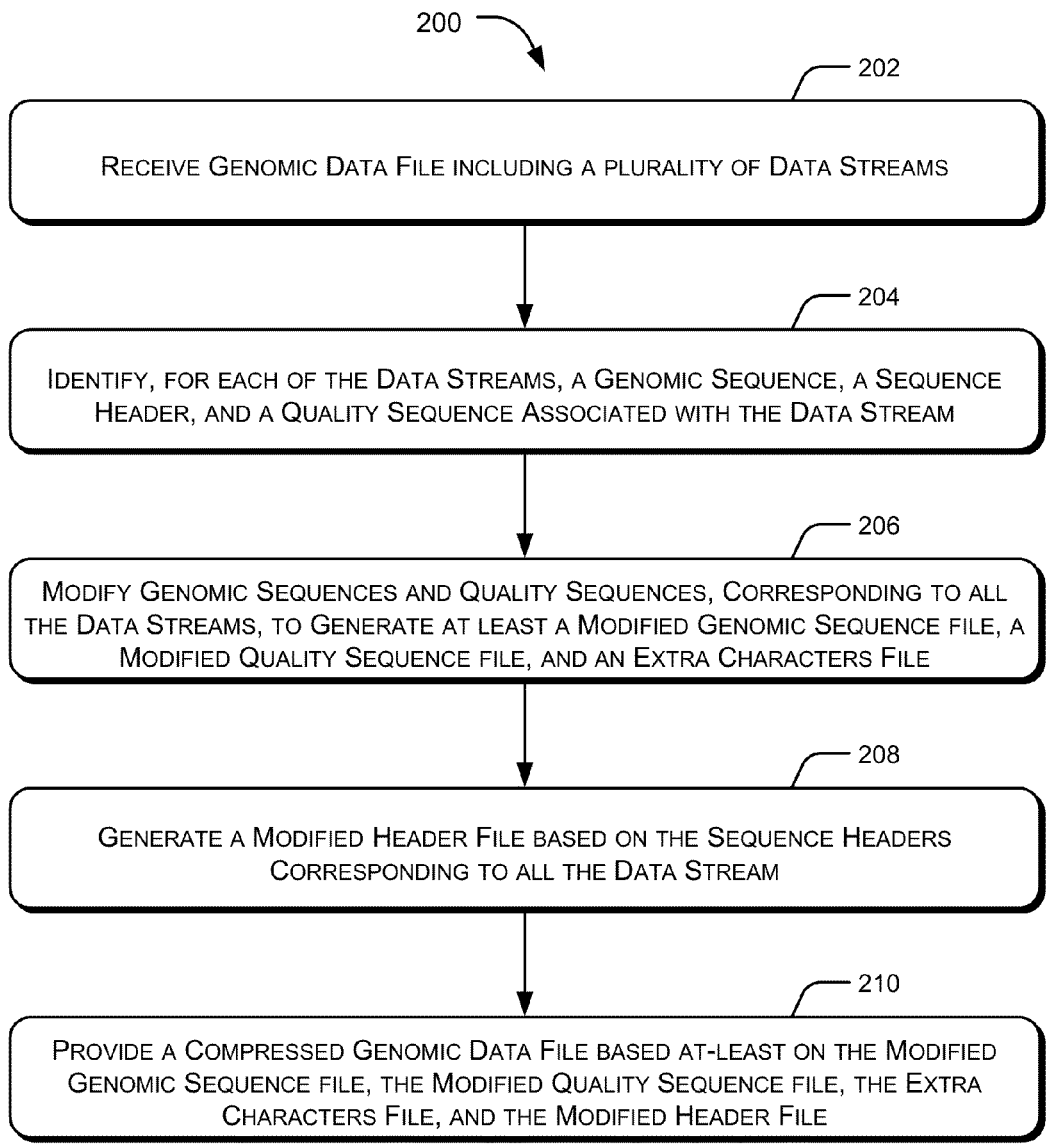
FIG. 2 illustrates a method for compression of a genomic data file, in accordance with an embodiment of the present subject matter.
Figure 3:
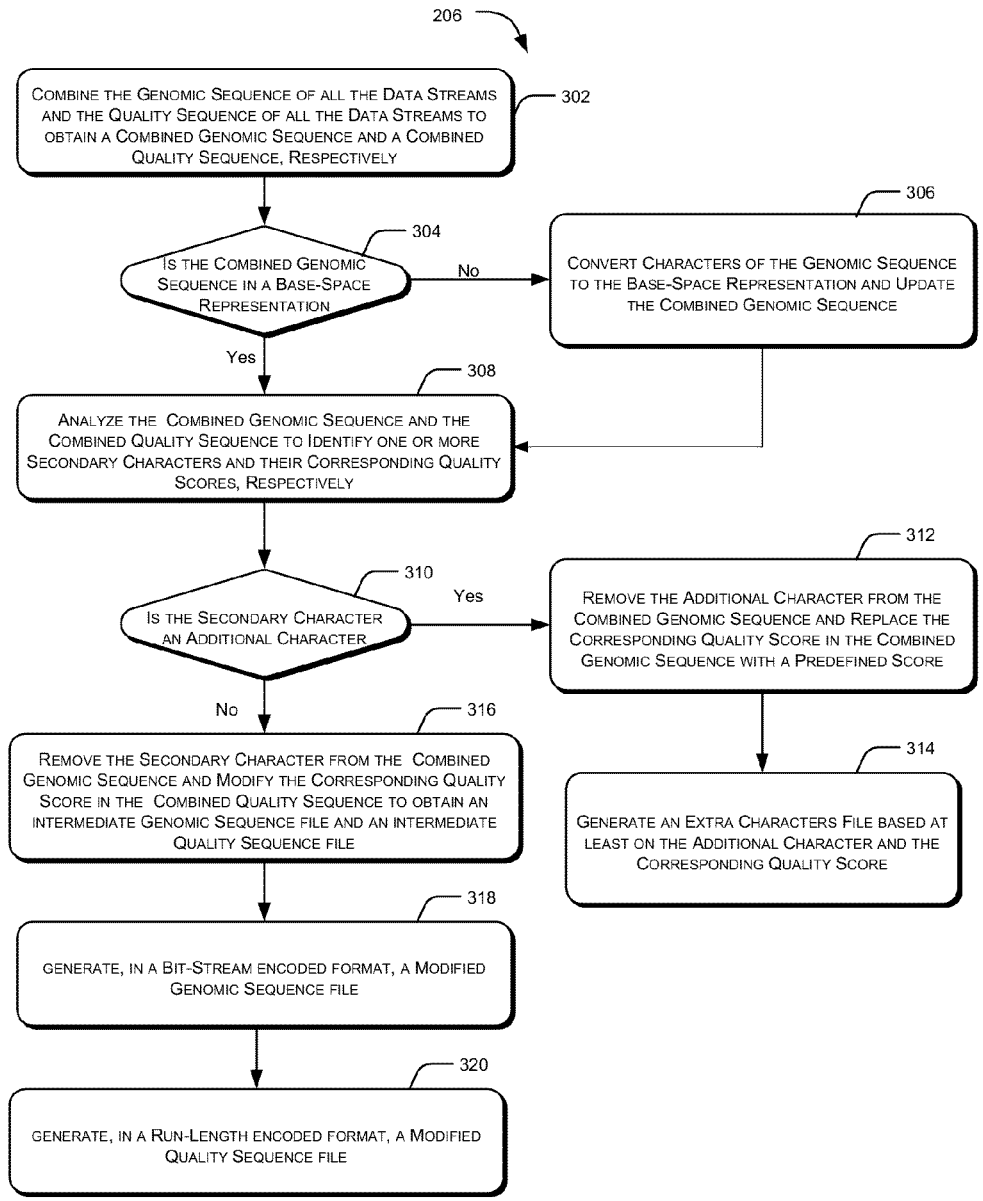
FIG. 3 illustrates a method of generating modified genomic sequence file, modified quality sequence file, and extra characters file for compressing the genomic data file, in accordance with an embodiment of the present subject matter.
Figure 4:
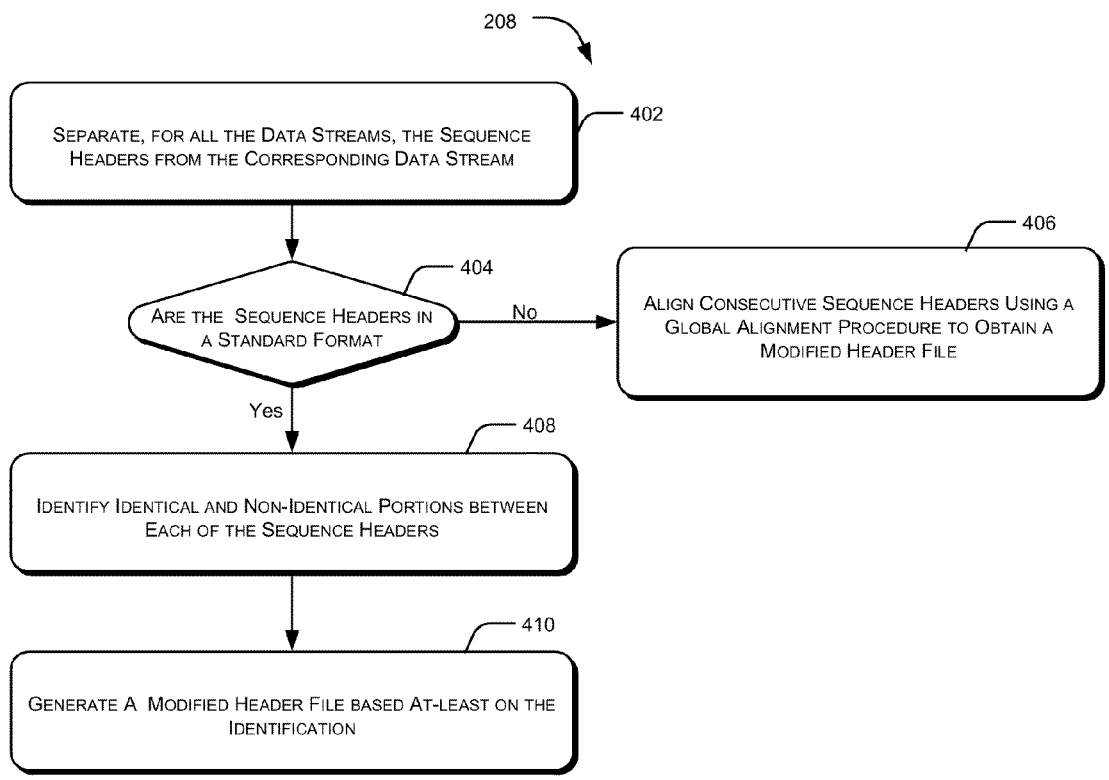
FIG. 4 illustrates a method of generating a modified header file for compressing the genomic data file, in accordance with an embodiment of the present subject matter.

FIG. 2 illustrates a method 200 for compressing a genomic data file, in accordance with an implementation of the present subject matter, FIG. 3 illustrates a method 206 for generating modified genomic sequence file and the modified quality sequence file, and FIG. 4 illustrates a method 208 for generating a modified header file according to an embodiment. The methods 200, 206, and 208 are implemented in computing device, such as the genomic data compression system 100.

The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network.

The order in which the methods are described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the methods can be implemented in any suitable hardware, software, firmware, or combination thereof.

At block 202, genomic data file, to be compressed, having a plurality of data streams is received, for example, by the system 100. In one implementation, the genomic data file is in a text-based file format, such as fastq and gff format. Further, each of the data stream includes a genomic sequence and a quality sequence corresponding to the genomic sequence. The genomic data file may thus include a plurality of genomic sequences and a corresponding plurality of quality sequences equal in number to the data stream. The genomic sequences may be, for example, nucleotide sequences, polypeptide sequences, DNA sequences, or RNA sequences. In an implementation, the genomic data file may be stored in the input data 118.

At block 204, for each of the data streams, a genomic sequence, a sequence header, and a quality sequence associated with the data stream are identified. In an implementation, the intermediate file generation module 112 may be configured to analyze the genomic data file to identify the sequence headers, the genomic sequences, and the quality sequences, corresponding to each of the data streams.

At block 206, the genomic sequences and the quality sequences, corresponding to all the data streams, are modified to generate at least a modified genomic sequence file, a modified quality sequence file, and an extra characters file. In one implementation, the genomic sequences and the quality sequences are analyzed to identify the primary characters, the secondary characters, and their corresponding quality scores. The secondary characters from the genomic sequences may be removed and the genomic sequences may be bit-stream encoded, for example, by the compression module 114, to obtain the modified genomic sequence file in a bit-stream encoded format. Further, quality scores corresponding to the secondary characters may be modified and the quality scores run-length encoded, for example, by the compression module 114 to obtain the modified quality sequence file in an ASCII encoded format. Further, information related to predetermined secondary characters may be saved in the extra characters file. The generation of the modified genomic sequence file, the modified quality sequence file, and the extra characters file may be further explained with reference to FIG. 3.

At block 208, a modified header file may be generated based on the sequence headers corresponding to all the data streams. In an example, the sequence headers corresponding to all the data streams are analyzed and modified by the compression module 114 to generate the modified header file, as will be explained in detail with reference to FIG. 4. Further, the compression module 114 may also generate an attribute file based on the header sequence.

At block 210, a compressed genomic data file is provided based at least on the modified genomic sequence file, the modified quality sequence file, the extra characters file, and the modified header file. In one implementation, the compression module 114 archives the modified header file, the modified genomic sequence file, the modified quality sequence file, the extra characters file, and the attribute file to produce the compressed genomic data file. Further, in order to facilitate an efficient processing and storing, the compression module 114 may further-compress all the files individually using any suitable compression technology and archive the files together to generate the compressed genomic data file. The compressed genomic data file may be obtained using any known archiving or compression technology, for example, the modified genomic sequence file may be further-compressed using LZMA compression technique. While, the modified header file, the modified quality sequence file, the extra characters file, and the attribute file may be further-compressed using PPMD compression technique. The compressed genomic data file thus includes all the details pertaining to not only the primary characters but also the sequence headers and secondary characters. Thus, the described method provides for loss-less compression of data. Further, the genomic data file is compressed without compromising on compression ratio and time, thereby making the described method efficient in terms of computational time and resources.

Referring to FIG. 3, the method 206 generates the modified genomic sequence file, the quality sequence file, and the extra characters file for compressing the genomic data file, in accordance with an embodiment of the present subject matter.

At block 302, the genomic sequences and the quality sequences of all the data streams are combined to obtain a combined genomic sequence and a combined quality sequence, respectively. In one implementation, the genomic sequences for all the data streams may be obtained and combined by, for example, the intermediate file generation module 112 to obtain the combined genomic sequence. Similarly, the quality sequences for all the data streams may be obtained and combined to obtain the combined quality sequence. The combined genomic sequence and the combined quality sequence may be saved in the compression data 120.

At block 304, a determination is made, for the combined genomic sequence, to ascertain whether the combined genomic sequence is in a base-space representation. For example, the intermediate file generation module 112 analyzes the combined genomic sequence, to ascertain whether the combined genomic sequence is in a base-space representation. If the combined genomic sequence is not in a base-space representation, which is the No path from the block 304, it converts characters of the genomic sequence to the base-space representation and updates the combined genomic sequence at block 306. For example, characters may be converted from the color-space representation to the base-space representation by the intermediate file generation module 112. From the block 306, the method proceeds to block 308, which is the 'Yes' path from the block 304.

At block 308, the combined genomic sequence and the combined quality sequence are analyzed to identify one or more secondary characters and their corresponding quality scores, respectively. In one implementation, the combined genomic sequence is analyzed to identify the secondary characters. For instance, in a nucleotide sequence, the non-ATGC characters, like 'Y', 'W', 'M', 'K', 'B', 'V', 'D', 'N', 'X', 'H', 'R', and 'S may be identified as the secondary characters. Further, the combined quality sequences may be analyzed by the intermediate file generation module 112 to identify, based on positions of the secondary characters in the combined genomic sequence, the quality scores corresponding to the secondary characters.

At block 310, a determination is made to ascertain whether the identified secondary character is an additional character. For example, the intermediate file generation module 112 analyzes the secondary characters and the corresponding quality scores, to ascertain whether the secondary character is an additional character. If the secondary character is an additional character, which is the 'Yes' path from the block 310, it removes the additional character from the combined genomic sequence and replaces the corresponding quality score in the combined quality sequence with a predefined score, at block 312. From the block 312, the method proceeds to block 314, where an extra characters file is generated using identity and quality scores for all the additional characters.

In case it is determined that the secondary character is not an additional character, which is the 'No' path from the block 310, the secondary character is removed from the combined genomic sequence and the corresponding quality score is modified in the combined quality sequence. An intermediate genomic sequence file and an intermediate quality sequence file are thus obtained at block 316.

At block 318, a modified genomic sequence file is generated in a bit-stream encoded format. In one implementation, the intermediate genomic sequence file may be encoded, for example, by the compression module 114 using a bit-stream encoding scheme to obtain the modified genomic sequence file.

At block 320 the intermediate quality sequence file may be analyzed to determine continuous stretches of similar quality scores, for example, using the compression module 114. The continuous stretches having a run-length, indicating the length of the continuous stretch, of more than a predetermined value may then be replaced by a single instance of the quality score and the run-length value to obtain the modified quality sequence file. The modified quality sequence file may be saved by the compression module 114 in the compression data 120.

Referring to FIG. 4, the method 208 generates a modified header file for compressing the genomic data file, in accordance with an embodiment of the present subject matter.

At block 402, the sequence headers corresponding to all the data streams are separated and combined to obtain a combined sequence header. In one implementation, the sequence headers for all the data streams may be obtained and combined by, for example, the intermediate file generation module 112 to obtain the combined sequence header.

At block 404, a determination is made to ascertain whether the sequence headers are in a standard format. For example, the compression module 114 analyzes the combined sequence header, to ascertain whether the sequence headers are in a standard format. If the sequence headers are not in a standard format, which is the 'No' path from the block 404, it aligns the consecutive sequence headers using a global alignment procedure to obtain a modified header file at block 406. In one implementation, identical and non-identical portions between consecutive sequence headers are identified by global-alignment. The identical and non-identical portions for each of the headers are subsequently indexed. For example, a first sequence header may be kept as a reference and all portions varying in the subsequent sequence header may be identified and indexed by the compression module 114. Similarly, all the sequence headers may be compared with the preceding sequence headers to obtain the modified header file by the intermediate file generation module 112 based at least on the indexing.

In case it is determined that the sequence headers are in the standard format, which is the 'Yes' path from the block 404, identical and non-identical portions between each of the sequence headers are identified at block 408. In one implementation, the compression module 114 may identify identical portions and non-identical portions for various sections, such as sequence identifier and sequencing experiment details of all the sequence headers.

At block 410, a modified header file is generated based at least on the identification of the identical and non-identical portions. In one implementation, the compression module 114 may index identical portions for the various sections of all the sequence headers and delta encode the non-identical portions. For instance, if the non-identical portions follow a consistent increasing or decreasing numerical pattern, the compression module 114 data may delta-encode the various sections based on the index and the non-identical portions to obtain the modified header file. Additionally, for genomic sequences having variable length the compression module 114 appends the length with the corresponding sequence header. The header file may then be saved in the compression data 120.

Although embodiments for compression of genomic data file have been described in language specific to structural features and/or methods, it is to be understood that the invention is not necessarily limited to the specific features or methods described. Rather, the specific features and methods are disclosed as exemplary embodiments for the compression of genomic data file.

We claim:

1. A computer-implemented method for compression of a genomic data file comprising:

identifying within the genomic data file, by a processor, sequence headers, genomic sequences and quality sequences associated with a plurality of data streams provided in the genomic data file, wherein each of the genomic sequences includes at least one of primary characters and secondary characters, wherein the genomic data file is obtained from a genomic data repository, and wherein the genomic data file is generated by sequencing genetic material obtained from one of a biological and an environmental sample;

removing, by the processor, the secondary characters from each of the genomic sequences to obtain an intermediate genomic sequence file;

in each of the quality sequences, modifying, by the processor, a quality score corresponding to the secondary character removed from corresponding genomic sequence to obtain an intermediate quality sequence file;

generating, by the processor, a modified genomic sequence file and a modified quality sequence file by modifying the intermediate genomic sequence file and the intermediate quality sequence file, respectively; and generating, by the processor, a compressed genomic data file, wherein the compressed genomic data file includes at least the modified genomic sequence file and the modified quality sequence file.

2. The computer-implemented method as claimed in claim 1, wherein the method further comprises modifying, by the processor, the sequence headers for generating a modified header file.

3. The computer-implemented method as claimed in claim 2, wherein the generating the modified header file comprises:
   determining whether each of the sequence headers conform to a standard format of sequence header representation; and
   generating an attributes file based at least on attributes related to the determined format.

4. The computer-implemented method as claimed in claim 3, wherein, for sequence headers conforming to the standard format, the generating the modified header file comprises:
   combining the sequence headers to obtain a combined sequence header;
   identifying, for each of the sequence headers, various sections of the sequence header;
   determining, for each of the various sections, identical and non-identical portions between each of the sequence headers;
   indexing the identical portions for each of the various sections;
   delta-encoding the various sections based on the indexing and the non-identical portions; and
   obtaining the modified header file based at least on the indexing and the delta-encoding.

5. The computer-implemented method as claimed in claim 3, wherein, for sequence headers not conforming to the standard format, the generating the modified header file comprises:
   combining the sequence headers to obtain a combined sequence header;
   identifying identical and non-identical portions between consecutive sequence headers by global-alignment;
   indexing the identical and non-identical portions for each of the headers; and
   obtaining the modified header file based at least on the indexing.

6. The computer-implemented method as claimed in claim 1, wherein the removing the secondary characters comprises:
   combining the genomic sequences to obtain a combined genomic sequence;
   determining whether the combined genomic sequence is in color-space representation;
   converting, based on the determining, each of the primary characters and the secondary characters to a base-space representation; and
   generating an attributes file having attributes related to color-space representation.

7. The computer-implemented method as claimed in claim 1, wherein the modifying the quality score comprises:
   combining the quality sequences to obtain a combined quality sequence;
   determining whether the secondary character is an additional character; and
   replacing, based on the determining, the quality score corresponding to the secondary character with a predefined score in the combined quality sequence.

8. The computer-implemented method as claimed in claim 1, wherein the modifying the quality score comprises:
   combining the quality sequences to obtain a combined quality sequence;
   determining whether the secondary character is an additional character; and
   encoding, based on the determining, the quality score corresponding to the secondary character using American standard code for information interchange (ASCII) encoding.

9. The computer-implemented method as claimed in claim 1, wherein the generating the modified genomic sequence file comprises bit-stream encoding the intermediate genomic sequence file to obtain the modified genomic sequence file.

10. The computer-implemented method as claimed in claim 1, wherein the generating the modified quality sequence file comprises:
    identifying one or more continuous stretches of similar quality score in the intermediate quality sequence file, wherein the one or more continuous stretches have a run-length of more than a predetermined value; and
    replacing, each of the one or more continuous stretches, with a single instance of the quality score and the run-length of the continuous stretches to obtain the modified quality sequence file in a run-length encoded format.

11. A genomic data compression system, the system comprising:
    a processor; and
    a memory coupled to the processor, the memory comprising:
       a intermediate file generation module configured to,
          identify within the genomic data file, sequence headers, genomic sequences and quality sequences associated with a plurality of data streams provided in a genomic data file, wherein each of the genomic sequences includes at least one of primary characters and secondary characters, wherein the genomic data file is obtained from a genomic data repository associated with the genomic data compression system, and wherein the genomic data file is generated by sequencing genetic material obtained from one of a biological and an environmental sample; and
          obtain at least an intermediate genomic sequence file, an intermediate quality sequence file, and an extra characters file based on the identification; and
       a compression module configured to,
          modify the intermediate genomic sequence file and the intermediate quality sequence file to generate a modified genomic sequence file and a modified quality sequence file, respectively;
          modify the sequence headers to create a modified header file; and
          generate a compressed genomic data file, wherein the compressed genomic data file includes at least the modified genomic sequence file, the modified header file, the extra characters file, and the modified quality sequence file.

12. The genomic data compression system as claimed in claim 11, wherein the intermediate file generation module is configured to,
   combine the genomic sequences to obtain a combined genomic sequence;
   determine whether the combined genomic sequence is in color-space representation;
   convert, based on the determination, each of the primary characters and the secondary characters to a base-space representation; and
   generate an attributes file based at least on attributes related to color-space representation.

13. The genomic data compression system as claimed in claim 11, wherein the intermediate file generation module is configured to,
   determine, for each of the secondary characters, whether the secondary character is an additional character;
   modify, in each of the quality sequences, a quality score corresponding to the secondary character to obtain the intermediate quality sequence file based on the determination; and
   remove the secondary characters from each of the genomic sequences to obtain the intermediate genomic sequence file.

14. The genomic data compression system as claimed in claim 11, wherein the compression module is configured to,
   identify one or more continuous stretches of similar quality score in the intermediate quality sequence file, wherein the one or more continuous stretches have a run-length greater than a predetermined value; and
   replace, each of the one or more continuous stretches, with a single instance of the quality score and the run-length to obtain the modified quality sequence file in a run-length encoded format.

15. The genomic data compression system as claimed in claim 11, wherein the compression module is configured to bit-stream encode the intermediate genomic sequence file to obtain the modified genomic sequence file.

16. A non-transitory computer-readable medium having embodied thereon a computer program for executing a method comprising:
   identifying within the genomic data file, sequence headers, genomic sequences and quality sequences associated with a plurality of data streams provided in a genomic data file, wherein each of the genomic sequences includes at least one of primary characters and secondary characters, wherein the genomic data file is obtained from a genomic data repository, and wherein the genomic data file is generated by sequencing genetic material obtained from one of a biological and an environmental sample;
   removing the secondary characters from each of the genomic sequences to obtain an intermediate genomic sequence file;
   modifying, in each of the quality sequences, a quality score corresponding to the secondary character to obtain an intermediate quality sequence file;
   generating a modified genomic sequence file and a modified quality sequence file by modifying the intermediate genomic sequence file and the intermediate quality sequence file, respectively; and
   generating a compressed genomic data file, wherein the compressed genomic data file includes at least the modified genomic sequence file and the modified quality sequence file.

17. The non-transitory computer readable medium as claimed in claim 16, wherein the removing the secondary character comprises:
   combining the genomic sequences to obtain a combined genomic sequence;
   determining whether the combined genomic sequence is in color-space representation;
   converting, based on the determining, each of the primary characters and the secondary characters to a base-space representation; and
   generating an attributes file having attributes related to color-space representation.

18. The non-transitory computer readable medium as claimed in claim 16, wherein the modifying comprises:
   combining the quality sequences to obtain a combined quality sequence;
   determining whether the secondary character is an additional character; and
   replacing, based on the determining, the quality score corresponding to the secondary character with a predefined score in the combined quality sequence.

* * * * *

SEQUENCE LISTING

```
<160> NUMBER OF SEQ ID NOS: 6

<210> SEQ ID NO 1
<211> LENGTH: 76
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (26)..(31)
<223> OTHER INFORMATION: n may be a secondary character
<220> FEATURE:
<221> NAME/KEY: misc_feature
<222> LOCATION: (33)..(34)
<223> OTHER INFORMATION: n may be a secondary character
<220> FEATURE:
<221> NAME/KEY: misc_feature
<222> LOCATION: (36)..(37)
<223> OTHER INFORMATION: n may be a secondary character
<220> FEATURE:
<221> NAME/KEY: misc_feature
<222> LOCATION: (39)..(39)
<223> OTHER INFORMATION: n may be a secondary character
<220> FEATURE:
<221> NAME/KEY: misc_feature
<222> LOCATION: (43)..(43)
<223> OTHER INFORMATION: n may be a secondary character
<220> FEATURE:
<221> NAME/KEY: misc_feature
<222> LOCATION: (45)..(51)
<223> OTHER INFORMATION: n may be a secondary character
<220> FEATURE:
<221> NAME/KEY: misc_feature
<222> LOCATION: (53)..(54)
<223> OTHER INFORMATION: n may be a secondary character
<220> FEATURE:
<221> NAME/KEY: misc_feature
<222> LOCATION: (56)..(56)
<223> OTHER INFORMATION: n may be a secondary character
<220> FEATURE:
<221> NAME/KEY: misc_feature
<222> LOCATION: (58)..(66)
<223> OTHER INFORMATION: n may be a secondary character
```

-continued

<400> SEQUENCE: 1
agttgatcca cctgaagaat taggannnnn nanntnngnc acncnnnnnn ngnnanannn     60
nnnnnnctat aaacca                                                    76

<210> SEQ ID NO 2
<211> LENGTH: 76
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (26)..(31)
<223> OTHER INFORMATION: n may be a secondary character
<220> FEATURE:
<221> NAME/KEY: misc_feature
<222> LOCATION: (33)..(34)
<223> OTHER INFORMATION: n may be a secondary character
<220> FEATURE:
<221> NAME/KEY: misc_feature
<222> LOCATION: (36)..(37)
<223> OTHER INFORMATION: n may be a secondary character
<220> FEATURE:
<221> NAME/KEY: misc_feature
<222> LOCATION: (39)..(39)
<223> OTHER INFORMATION: n may be a secondary character
<220> FEATURE:
<221> NAME/KEY: misc_feature
<222> LOCATION: (43)..(43)
<223> OTHER INFORMATION: n may be a secondary character
<220> FEATURE:
<221> NAME/KEY: misc_feature
<222> LOCATION: (45)..(51)
<223> OTHER INFORMATION: n may be a secondary character
<220> FEATURE:
<221> NAME/KEY: misc_feature
<222> LOCATION: (53)..(54)
<223> OTHER INFORMATION: n may be a secondary character
<220> FEATURE:
<221> NAME/KEY: misc_feature
<222> LOCATION: (56)..(56)
<223> OTHER INFORMATION: n may be a secondary character
<220> FEATURE:
<221> NAME/KEY: misc_feature
<222> LOCATION: (58)..(66)
<223> OTHER INFORMATION: n may be a secondary character

<400> SEQUENCE: 2
gggtatgttc tgttctcctg gccatnnnnn nanncnngnc ttncnnnnnn ngnntnannn     60
nnnnnntgtc actgtc                                                    76

<210> SEQ ID NO 3
<211> LENGTH: 76
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (26)..(31)
<223> OTHER INFORMATION: n may be a secondary character
<220> FEATURE:
<221> NAME/KEY: misc_feature
<222> LOCATION: (33)..(34)
<223> OTHER INFORMATION: n may be a secondary character
<220> FEATURE:
<221> NAME/KEY: misc_feature
<222> LOCATION: (36)..(37)
<223> OTHER INFORMATION: n may be a secondary character
<220> FEATURE:
<221> NAME/KEY: misc_feature
<222> LOCATION: (39)..(39)

<223> OTHER INFORMATION: n may be a secondary character
<220> FEATURE:
<221> NAME/KEY: misc_feature
<222> LOCATION: (43)..(43)
<223> OTHER INFORMATION: n may be a secondary character
<220> FEATURE:
<221> NAME/KEY: misc_feature
<222> LOCATION: (45)..(51)
<223> OTHER INFORMATION: n may be a secondary character
<220> FEATURE:
<221> NAME/KEY: misc_feature
<222> LOCATION: (53)..(54)
<223> OTHER INFORMATION: n may be a secondary character
<220> FEATURE:
<221> NAME/KEY: misc_feature
<222> LOCATION: (56)..(56)
<223> OTHER INFORMATION: n may be a secondary character
<220> FEATURE:
<221> NAME/KEY: misc_feature
<222> LOCATION: (58)..(59)
<223> OTHER INFORMATION: n may be a secondary character
<220> FEATURE:
<221> NAME/KEY: misc_feature
<222> LOCATION: (61)..(66)
<223> OTHER INFORMATION: n may be a secondary character

<400> SEQUENCE: 3
tgccttcagc ccaaaaagcc cacgcnnnnn nanntnncnc ctntnnnnnn ntnncncnnt    60
nnnnnntaac tctcca                                                  76

<210> SEQ ID NO 4
<211> LENGTH: 76
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (26)..(31)
<223> OTHER INFORMATION: n may be a secondary character
<220> FEATURE:
<221> NAME/KEY: misc_feature
<222> LOCATION: (33)..(34)
<223> OTHER INFORMATION: n may be a secondary character
<220> FEATURE:
<221> NAME/KEY: misc_feature
<222> LOCATION: (36)..(37)
<223> OTHER INFORMATION: n may be a secondary character
<220> FEATURE:
<221> NAME/KEY: misc_feature
<222> LOCATION: (39)..(39)
<223> OTHER INFORMATION: n may be a secondary character
<220> FEATURE:
<221> NAME/KEY: misc_feature
<222> LOCATION: (43)..(43)
<223> OTHER INFORMATION: n may be a secondary character
<220> FEATURE:
<221> NAME/KEY: misc_feature
<222> LOCATION: (45)..(51)
<223> OTHER INFORMATION: n may be a secondary character
<220> FEATURE:
<221> NAME/KEY: misc_feature
<222> LOCATION: (54)..(54)
<223> OTHER INFORMATION: n may be a secondary character
<220> FEATURE:
<221> NAME/KEY: misc_feature
<222> LOCATION: (56)..(56)
<223> OTHER INFORMATION: n may be a secondary character
<220> FEATURE:
<221> NAME/KEY: misc_feature
<222> LOCATION: (58)..(58)
<223> OTHER INFORMATION: n may be a secondary character
<220> FEATURE:
<221> NAME/KEY: misc_feature
<222> LOCATION: (61)..(66)
<223> OTHER INFORMATION: n may be a secondary character

<400> SEQUENCE: 4
ctgcgctccc tccctccacc cacttnnnnn ncnncnntna ctntnnnnnn nctncncncc      60
nnnnnnctat tcccca      76

<210> SEQ ID NO 5
<211> LENGTH: 304
<212> TYPE: DNA
<213> ORGANISM: Unknown
<220> FEATURE:
<223> OTHER INFORMATION: Unknown genomic sequence
<220> FEATURE:
<221> NAME/KEY: misc_feature
<222> LOCATION: (26)..(31)
<223> OTHER INFORMATION: n may be a secondary character
<220> FEATURE:
<221> NAME/KEY: misc_feature
<222> LOCATION: (33)..(34)
<223> OTHER INFORMATION: n may be a secondary character
<220> FEATURE:
<221> NAME/KEY: misc_feature
<222> LOCATION: (36)..(37)
<223> OTHER INFORMATION: n may be a secondary character
<220> FEATURE:
<221> NAME/KEY: misc_feature
<222> LOCATION: (39)..(39)
<223> OTHER INFORMATION: n may be a secondary character
<220> FEATURE:
<221> NAME/KEY: misc_feature
<222> LOCATION: (43)..(43)
<223> OTHER INFORMATION: n may be a secondary character
<220> FEATURE:
<221> NAME/KEY: misc_feature
<222> LOCATION: (45)..(51)
<223> OTHER INFORMATION: n may be a secondary character
<220> FEATURE:
<221> NAME/KEY: misc_feature
<222> LOCATION: (53)..(54)
<223> OTHER INFORMATION: n may be a secondary character
<220> FEATURE:
<221> NAME/KEY: misc_feature
<222> LOCATION: (56)..(56)
<223> OTHER INFORMATION: n may be a secondary character
<220> FEATURE:
<221> NAME/KEY: misc_feature
<222> LOCATION: (58)..(66)
<223> OTHER INFORMATION: n may be a secondary character
<220> FEATURE:
<221> NAME/KEY: misc_feature
<222> LOCATION: (102)..(107)
<223> OTHER INFORMATION: n may be a secondary character
<220> FEATURE:
<221> NAME/KEY: misc_feature
<222> LOCATION: (109)..(110)
<223> OTHER INFORMATION: n may be a secondary character
<220> FEATURE:
<221> NAME/KEY: misc_feature
<222> LOCATION: (112)..(113)
<223> OTHER INFORMATION: n may be a secondary character
<220> FEATURE:
<221> NAME/KEY: misc_feature
<222> LOCATION: (115)..(115)
<223> OTHER INFORMATION: n may be a secondary character
<220> FEATURE:
<221> NAME/KEY: misc_feature
<222> LOCATION: (119)..(119)
<223> OTHER INFORMATION: n may be a secondary character
<220> FEATURE:
<221> NAME/KEY: misc_feature
<222> LOCATION: (121)..(127)
<223> OTHER INFORMATION: n may be a secondary character
<220> FEATURE:
<221> NAME/KEY: misc_feature
<222> LOCATION: (129)..(130)
<223> OTHER INFORMATION: n may be a secondary character
<220> FEATURE:

```
<221> NAME/KEY: misc_feature
<222> LOCATION: (132)..(132)
<223> OTHER INFORMATION: n may be a secondary character
<220> FEATURE:
<221> NAME/KEY: misc_feature
<222> LOCATION: (134)..(142)
<223> OTHER INFORMATION: n may be a secondary character
<220> FEATURE:
<221> NAME/KEY: misc_feature
<222> LOCATION: (178)..(183)
<223> OTHER INFORMATION: n may be a secondary character
<220> FEATURE:
<221> NAME/KEY: misc_feature
<222> LOCATION: (185)..(186)
<223> OTHER INFORMATION: n may be a secondary character
<220> FEATURE:
<221> NAME/KEY: misc_feature
<222> LOCATION: (188)..(189)
<223> OTHER INFORMATION: n may be a secondary character
<220> FEATURE:
<221> NAME/KEY: misc_feature
<222> LOCATION: (191)..(191)
<223> OTHER INFORMATION: n may be a secondary character
<220> FEATURE:
<221> NAME/KEY: misc_feature
<222> LOCATION: (195)..(195)
<223> OTHER INFORMATION: n may be a secondary character
<220> FEATURE:
<221> NAME/KEY: misc_feature
<222> LOCATION: (197)..(203)
<223> OTHER INFORMATION: n may be a secondary character
<220> FEATURE:
<221> NAME/KEY: misc_feature
<222> LOCATION: (205)..(206)
<223> OTHER INFORMATION: n may be a secondary character
<220> FEATURE:
<221> NAME/KEY: misc_feature
<222> LOCATION: (208)..(208)
<223> OTHER INFORMATION: n may be a secondary character
<220> FEATURE:
<221> NAME/KEY: misc_feature
<222> LOCATION: (210)..(211)
<223> OTHER INFORMATION: n may be a secondary character
<220> FEATURE:
<221> NAME/KEY: misc_feature
<222> LOCATION: (213)..(218)
<223> OTHER INFORMATION: n may be a secondary character
<220> FEATURE:
<221> NAME/KEY: misc_feature
<222> LOCATION: (254)..(259)
<223> OTHER INFORMATION: n may be a secondary character
<220> FEATURE:
<221> NAME/KEY: misc_feature
<222> LOCATION: (261)..(262)
<223> OTHER INFORMATION: n may be a secondary character
<220> FEATURE:
<221> NAME/KEY: misc_feature
<222> LOCATION: (264)..(265)
<223> OTHER INFORMATION: n may be a secondary character
<220> FEATURE:
<221> NAME/KEY: misc_feature
<222> LOCATION: (267)..(267)
<223> OTHER INFORMATION: n may be a secondary character
<220> FEATURE:
<221> NAME/KEY: misc_feature
<222> LOCATION: (271)..(271)
<223> OTHER INFORMATION: n may be a secondary character
<220> FEATURE:
<221> NAME/KEY: misc_feature
<222> LOCATION: (273)..(279)
<223> OTHER INFORMATION: n may be a secondary character
<220> FEATURE:
<221> NAME/KEY: misc_feature
<222> LOCATION: (282)..(282)
<223> OTHER INFORMATION: n may be a secondary character
<220> FEATURE:
<221> NAME/KEY: misc_feature
<222> LOCATION: (284)..(284)
<223> OTHER INFORMATION: n may be a secondary character
```

```
<220> FEATURE:
<221> NAME/KEY: misc_feature
<222> LOCATION: (286)..(286)
<223> OTHER INFORMATION: n may be a secondary character
<220> FEATURE:
<221> NAME/KEY: misc_feature
<222> LOCATION: (289)..(294)
<223> OTHER INFORMATION: n may be a secondary character

<400> SEQUENCE: 5
agttgatcca cctgaagaat taggannnnn nanntnngnc acncnnnnnn ngnnanannn     60
nnnnnnctat aaaccagggt atgttctgtt ctcctggcca tnnnnnnann cnngncttnc    120
nnnnnnngnn tnannnnnnn nntgtcactg tctgccttca gcccaaaaag cccacgcnnn    180
nnnanntnnc ncctntnnnn nnntnncncn ntnnnnnnta actctccact gcgctccctc    240
cctccaccca cttnnnnnnc nncnntnact ntnnnnnnnc tncncnccnn nnnnctattc    300
ccca                                                                304

<210> SEQ ID NO 6
<211> LENGTH: 1171
<212> TYPE: DNA
<213> ORGANISM: Unknown
<220> FEATURE:
<223> OTHER INFORMATION: Unknown genomic sequence

<400> SEQUENCE: 6
ggggcggggg cggcgcggcg gcgcgcccgg gcggggcccg gcgccggcgg ccgccggggg     60
cgcgcgcccg gggccccgcc gggcgcgcgg ccggccgcgg gggggcggg ggcggccccg    120 ccgcccgggc ccgcgccgcg ccgccggccg gccggggcg gccggcgggg cgcggccgcc    180
ccgcgggcgg ggggccggcg gccgcgccgg gccccgcgcg gcgggccggg gccgcccggc    240
cggcgccgcc cgcgggccgc ggccccgcg cgcggcgggc cgcgggccgc gccccccggc    300
ggcggcggcc gcgggccgcc ccccgccggc gggcgcgggg ggccccgcg gggcccgggc    360 ggggcccggg cgccggcggc cgccggggc gcgcgccccc cgcccggcgg ccgccccgcg    420
ccgccgcccg ggcgggccgg ccgcgcgggc cgcgggggggc gccggcgggc gggcggggc    480 gcgggcggcc ccgccggcg cgcgccgcc ggccgcgccg cccccccggc gcgcggccgc    540
gcccgcccgg gggccggcc ccccccccg ggggggcgcg ccggcgcgc cgcccgcgcc    600 cgcgcggggc cgcgcgggcc gggcgcgccc ggcggcgcgg gccggccgcc ggcggcgcgg    660
cggggcggcc ccgggcggcg ccgcggggcg cgccgcggcc ggccggcccg cggccgccgg    720
gcggcgcccg cgcggccgcc ccgccgcggg cgccgcgcgc gcgcgcggcc ccgccccggg    780
cggccgcccc gggcgccccg cgcgcgcccg cgcggcgccc ggggccggcg ccggcggcgg    840 cgccggcgg cgggcgccccc ggccgccccc gccgcggcgg cggccgcccc gccgcgcgcc    900
cgccccgccc gggccggcgg cccgccggcg ccgggcggcg cgcgcgccgc ccgggggggcg    960 gcgcggcggg ggcgcggcgg gcggccggcg ggcggcgcgc gcgcggcgc cgcccgccgc   1020 gcgcccccggc gccgcggggc gcgccccgcg cggcggccgc cggccgcccc cgcgccggcg   1080
ccggcgcgcc cgcggggggcg ccggcccccc ggcgccccgc gcgcgccggc gggcgggggcg   1140 gggcgcgcgc gcgccgcccc ggccccggcg c                                  1171
```